United States Patent
He et al.

(10) Patent No.: US 11,680,039 B2
(45) Date of Patent: Jun. 20, 2023

(54) COMPOUNDS CONTAINING CYCLIC STRUCTURAL ELEMENTS, URETHANE/UREIDO LINKAGES AND A FREE RADICAL-POLYMERIZABLE FUNCTIONAL GROUP

(71) Applicant: ARKEMA FRANCE, Colombes (FR)

(72) Inventors: Yuhong He, Honey Brook, PA (US); Sumeet Jain, Chester Springs, PA (US); William C. Wolf, Philadelphia, PA (US); Jeffrey A. Klang, West Chester, PA (US); Brendan T. McGrail, Phoenixville, PA (US)

(73) Assignee: Arkema France, Colombes (FR)

( * ) Notice: Subject to any disclaimer, the term of this patent is extended or adjusted under 35 U.S.C. 154(b) by 1071 days.

(21) Appl. No.: 16/323,813

(22) PCT Filed: Jul. 6, 2017

(86) PCT No.: PCT/EP2017/066961
§ 371 (c)(1),
(2) Date: Feb. 7, 2019

(87) PCT Pub. No.: WO2018/028903
PCT Pub. Date: Feb. 15, 2018

(65) Prior Publication Data
US 2021/0238128 A1    Aug. 5, 2021

Related U.S. Application Data

(60) Provisional application No. 62/372,859, filed on Aug. 10, 2016.

(51) Int. Cl.
| | |
|---|---|
| *C07C 271/24* | (2006.01) |
| *B33Y 70/10* | (2020.01) |
| *C07C 263/02* | (2006.01) |
| *C08G 18/32* | (2006.01) |
| *C09D 11/101* | (2014.01) |
| *B33Y 70/00* | (2020.01) |
| *C07C 269/02* | (2006.01) |
| *C08G 18/67* | (2006.01) |
| *C08G 18/75* | (2006.01) |
| *C08G 18/81* | (2006.01) |
| *B33Y 10/00* | (2015.01) |
| *B29C 64/106* | (2017.01) |
| *B29K 75/00* | (2006.01) |

(52) U.S. Cl.
CPC ............ *C07C 271/24* (2013.01); *B33Y 70/00* (2014.12); *C07C 269/02* (2013.01); *C08G 18/3212* (2013.01); *C08G 18/672* (2013.01); *C08G 18/755* (2013.01); *C08G 18/8175* (2013.01); *C09D 11/101* (2013.01); *B29C 64/106* (2017.08); *B29K 2075/00* (2013.01); *B33Y 10/00* (2014.12); *C07C 2601/16* (2017.05); *C07C 2603/68* (2017.05)

(58) Field of Classification Search
CPC . C07C 271/24; C07C 269/02; C07C 2601/16; C07C 2603/68; C07C 2601/14; B33Y 70/00; B33Y 10/00; C08G 18/3212; C08G 18/672; C08G 18/755; C08G 18/8175; C09D 11/101; B29C 64/106; B29K 2075/00; B32B 2255/06; B32B 2255/08; B32B 2255/10; B32B 2255/12; B32B 2255/26; B32B 2307/50; B32B 2307/546; B32B 9/025; B32B 9/04; B32B 9/041; B32B 9/042; B32B 9/045; B32B 9/06; B32B 15/04; B32B 15/043; B32B 15/08; B32B 15/085; B32B 15/09; B32B 15/10; B32B 15/12; B32B 21/04; B32B 21/042; B32B 21/06; B32B 21/08; B32B 27/06; B32B 27/08; B32B 27/10; B32B 27/302; B32B 27/32; B32B 27/36; B32B 29/002; B32B 29/005; B32B 29/08; B32B 7/12
See application file for complete search history.

(56) References Cited

U.S. PATENT DOCUMENTS

| | | | |
|---|---|---|---|
| 3,867,152 A | 2/1975 | Priem et al. | |
| 5,567,761 A | * 10/1996 | Song ................ | C09D 133/062 525/131 |

(Continued)

FOREIGN PATENT DOCUMENTS

| | | |
|---|---|---|
| JP | H0480212 A | 3/1992 |
| JP | H0790043 A | 4/1995 |

(Continued)

OTHER PUBLICATIONS

Schulz, R.C. and Hartmann, H., "Dihydropyran-Derivate durch Dien-Synthesen von alpha.beta-ungesattigten Carbonylverbindungen mit N-Vinyl-Verbindungen", Chemische Berichte Jaheg. 95, May 16, 1962, pp. 2735-2741.

(Continued)

*Primary Examiner* — Jessica M Roswell
(74) *Attorney, Agent, or Firm* — Christopher R. Lewis

(57) ABSTRACT

Compounds useful for formulating inks, 3D printing resins, molding resins, coatings, sealants and adhesives which exhibit reduced shrinkage stress and high hardness and stiffness when cured are described which include a single free radical-polymerizable functional group, one or more urethane and/or ureido linkages and one or more cyclic structural elements per molecule.

26 Claims, No Drawings

(56) References Cited

U.S. PATENT DOCUMENTS

| | | | |
|---|---|---|---|
| 2010/0036013 A1* | 2/2010 | Roelle | C07C 323/36 |
| | | | 522/174 |
| 2012/0296003 A1 | 11/2012 | Naruse et al. | |
| 2013/0199818 A1* | 8/2013 | Uchida | H01B 3/44 |
| | | | 522/42 |
| 2014/0154628 A1* | 6/2014 | Nagoshi | C08G 59/1455 |
| | | | 430/280.1 |
| 2018/0179445 A1* | 6/2018 | Inada | C08L 75/08 |

FOREIGN PATENT DOCUMENTS

| | | |
|---|---|---|
| JP | 2006213746 A | 8/2006 |
| WO | 2009053305 A1 | 4/2009 |

OTHER PUBLICATIONS

Rolf C. Schulz and Heinrich Hartmann, "Dihydropyran Derivatives through diene syntheses of alpha,beta-unsaturated carbonyl compounds with N-vinyl compounds", Institute of Organic Chemistry, University of Mainz, May 16, 1962, pp. 2735-2744.

\* cited by examiner

COMPOUNDS CONTAINING CYCLIC STRUCTURAL ELEMENTS, URETHANE/UREIDO LINKAGES AND A FREE RADICAL-POLYMERIZABLE FUNCTIONAL GROUP

CROSS-REFERENCE TO RELATED APPLICATIONS

This application is a U.S. national stage application under 35 U.S.C. § 371 of PCT/EP2017/066961, filed Jul. 6, 2017, which claims the benefit of U.S. patent application No. 62/372,859, filed Aug. 10, 2016.

FIELD OF INVENTION

The present invention relates to compounds capable of being cured by free radical polymerization, methods for preparing such compounds, as well as curable and cured compositions containing or based on such compounds, such as coatings, inks, adhesives, molding resins and 3D printing resins.

BACKGROUND OF THE INVENTION

For some time now, it has been recognized that urethane acrylates demonstrate improved mechanical properties over traditional acrylic pre-polymers; such compounds have therefore been the premier oligomer employed in the radiation (e.g., UV) curable industry. While formulations based on highly functionalized urethane acrylates (i.e., compounds containing two or more acrylate groups per molecule) demonstrate fast cure rates and high strength when cured, they have the significant disadvantage of exhibiting high shrinkage stress. The stress induced as a result of shrinkage during cure (polymerization) greatly reduces the degree of impact strength and dimensional stability in cured formulations containing such highly functionalized urethane acrylates. These attributes are particularly desirable in end-use applications such as three dimensional (3D) printing resin formulations. For these reasons, it would be desirable to develop alternative compounds capable of being used in radiation-curable formulations that deliver high hardness and stiffness without a high degree of shrinkage.

SUMMARY OF THE INVENTION

The inventors have discovered a class of compounds which, when incorporated into compositions which are to be cured by means of free radical polymerization, impart high hardness and stiffness to the cured compositions while at the same time reducing or minimizing the extent of shrinkage exhibited by the compositions during curing, particularly as compared to compositions based on conventional highly functionalized urethane acrylates. These compounds (which sometimes for convenience will be referred to herein as the "inventive monofunctional compounds") are characterized by having a single free radical-polymerizable functional group (e.g., an ethylenically unsaturated functional group such as an acrylate, methacrylate, vinyl or ally group) per molecule, at least one cyclic structural element (such as a tricyclodecane moiety) per molecule and at least two urethane (—O—C(=O)—NH—) and/or ureido (—NH—C(=O)—NH—) linkages per molecule. Without wishing to be bound by theory, it is believed that having a single reactive site helps to reduce the amount of shrinkage which occurs during curing of a composition containing such a compound, while the presence of urethane/ureido linkages (which are capable of participating in hydrogen bonding) and the cyclic structural element(s) raise the Tg (glass transition temperature) and/or stiffness (e.g., modulus) of the cured composition.

Various non-limiting aspects of the present invention may be summarized as follows:

Aspect 1: A compound having a structure in accordance with Formula (I):

$$Q\text{-}(R^1Z^1)_m\text{—}RZ \qquad (I)$$

wherein Q is a moiety containing a single free radical-polymerizable functional group, R is a urethane/ureido-containing structural unit, Z is a monovalent moiety containing at least one cyclic structural element, each $R^1$, if present, is independently selected to be a urethane/ureido-containing structural unit which is the same as or different from R, each $Z^1$, if present, is independently selected to be a divalent moiety containing at least one cyclic structural element, and m is 0 or an integer of 1 or more.

Aspect 2: The compound of Aspect 1, wherein the single free radical-polymerizable functional group in Q is a monoethylenically unsaturated functional group, in particular having a carbon-carbon double bond which is alpha to a carbonyl group.

Aspect 3: The compound of Aspect 1 or 2, wherein the single free radical-polymerizable functional group in Q is a functional group having a carbon-carbon double bond which is alpha to a carbonyl group.

Aspect 4: The compound of Aspect 1 to 3, wherein the single free radical-polymerizable functional group in Q is selected from the group consisting of allyl groups and (meth)acrylate groups.

Aspect 5: The compound of Aspect 1 to 4, wherein Q has structure $H_2C=C(R^2)C(=O)—O—R^3—$, with $R^2=H$, $CH_3$, or $CH_2CH_3$ and $R^3=$ a $C_2$ to $C_6$ linear or branched alkylene group, an oligoether moiety or an oligoester moiety.

Aspect 6: The compound of Aspect 1 to 4, wherein Q has structure $H_2C=CH—C(=O)OCH_2CH_2—$.

Aspect 7: The compound of any one of Aspects 1-6, wherein m is 0 or from 1 to 10.

Aspect 8: The compound of any one of Aspects 1-7, wherein m is an integer of from 1 to 10.

Aspect 9: The compound of any one of Aspects 1-8, wherein Z is a monovalent moiety containing at least one cyclic structural element selected from the group consisting of aromatic groups and alicyclic groups.

Aspect 10: The compound of any one of Aspects 1-9, wherein Z is a monovalent moiety containing at least one alicyclic structural element selected from the group consisting of monocyclic, bicyclic, tricyclic, tetracyclic, pentacyclic and hexacyclic hydrocarbon radicals.

Aspect 11: The compound of anyone of Aspects 1-10, wherein Z is a monovalent moiety containing a tricyclodecane radical, in particular having structure —$CH_2$-TCD with TCD being a tricyclodecane radical.

Aspect 12: The compound of any one of Aspects 1-11, wherein Z has structure —$CH_2$-TCD with TCD being a tricyclodecane radical.

Aspect 13: The compound of Aspect 1 to 12, wherein m is an integer of 1 or greater (than 1) and each $Z^1$ independently is a divalent moiety containing at least one cyclic structural element selected from the group consisting of aromatic groups and alicyclic groups.

Aspect 14: The compound of Aspect 1 to 13, wherein m is an integer of 1 or more and each $Z^1$ independently is a divalent moiety containing at least one alicyclic structural element selected from the group consisting of monocyclic, bicyclic, tricyclic, tetracyclic, pentacyclic and hexacyclic hydrocarbon radicals.

Aspect 15: The compound of Aspect 1 to 14, wherein m is an integer of 1 or more and each $Z^1$ independently is a divalent moiety containing a tricyclodecane radical, in particular, having structure —$CH_2$-TCD-$CH_2$— with TCD being a tricyclodecane radical.

Aspect 16: The compound of Aspect 1 to 15, wherein m is an integer of 1 or more (interger higher than 1) and each $Z^1$ independently has structure —$CH_2$-TCD-$CH_2$— with TCD being a tricyclodecane radical.

Aspect 17: The compound of any one of Aspects 1-16, wherein each R and $R^1$, if present, independently has structure —O—C(=O)NH—$R^3$—NH—C(=O)—O—, with $R^3$ being a divalent hydrocarbon radical, in particular selected from the group consisting of alkylene radicals, aliphatic ring-containing radicals and aromatic ring-containing radicals.

Aspect 18: The compound of any one of Aspects 1-17, wherein each R and $R^1$, if present, independently has structure —O—C(=O)NH—$R^3$—NH—C(=O)—O—, with $R^3$ being a divalent hydrocarbon radical selected from the group consisting of alkylene radicals, aliphatic ring-containing radicals and aromatic ring-containing radicals.

Aspect 19: A curable composition comprised of at least one compound in accordance with any one of Aspects 1-18 and at least one additional ethylenically unsaturated monomer or oligomer.

Aspect 20: The curable composition of Aspect 19, wherein the at least one additional ethylenically unsaturated monomer or oligomer includes at least one compound selected from the group consisting of (meth)acrylates, in particular selected from the group consisting of cyclic, linear and branched mono-, di- and tri-(meth)acrylate-functionalized monomers and oligomers.

Aspect 21: The curable composition of Aspect 19 or 20, wherein the at least one additional ethylenically unsaturated monomer or oligomer includes at least one compound selected from the group consisting of cyclic, linear and branched mono-, di- and tri-(meth)acrylate-functionalized monomers and oligomers.

Aspect 22: The curable composition of any one of Aspects 19-21, additionally comprising at least one additive selected from the group consisting of initiators, stabilizers and fillers.

Aspect 23: A cured composition which is the reaction product of (product which results from) the (cure of the) curable composition of any one of Aspects 19-22.

Aspect 24: An article comprising a cured composition in accordance with Aspect 23.

Aspect 25: The article of Aspect 24, wherein the article is a three-dimensional article, a coated article, a laminated article or a printed article.

Aspect 26: A method of making a compound in accordance with Aspect 1 to 18, comprising the steps of:
a) reacting a mono-hydroxyl or mono-amino functional compound containing a single free radical-polymerizable functional group with a diisocyanate in a stoichiometry effective to yield an intermediate product which is a 1:1 adduct of the mono-hydroxyl or mono-amino functional compound containing a single free radical-polymerizable functional group and the diisocyanate and which contains a single free radical-polymerizable functional group, a single isocyanate group and a urethane or ureido linkage;
b) reacting the intermediate product with a mono-hydroxyl or mono-amino functional compound containing at least one cyclic structural element.

Aspect 27: A method of making a compound in accordance with Aspect 1 to 18, comprising the steps of:
a) reacting i) a mono-hydroxyl or mono-amino functional compound containing a single free radical-polymerizable functional group, ii) a diisocyanate and iii) a di-hydroxyl, di-amino or mono-hydroxy and mono-amino functional compound containing at least one cyclic structural element in a stoichiometry effective to yield an intermediate product which is a 1:X:Y adduct of the mono-hydroxyl or mono-amino functional compound containing a single free radical-polymerizable functional group, the diisocyanate and the di-hydroxyl, di-amino or mono-hydroxy and mono-amino functional compound containing at least one cyclic structural element and which contains a single free radical-polymerizable functional group, a single isocyanate group and two or more urethane or ureido linkages, wherein X is an integer of 1 or more and represents the number of moles of di-hydroxyl, di-amino or mono-hydroxy and mono-amino functional compound containing at least one cyclic structural element incorporated in the adduct per mole of mono-hydroxyl or mono-amino functional compound containing a single free radical-polymerizable functional group, and Y=X+1 and represents the number of moles of diisocyanate incorporated in the adduct per mole of mono-hydroxyl or mono-amino functional compound containing a single free radical-polymerizable functional group;
b) reacting the intermediate product with a mono-hydroxyl or mono-amino functional compound containing at least one cyclic structural element.

Aspect 28: A method of making a compound in accordance with Aspect 1 to 18, comprising the steps of:
a) reacting a mono-hydroxyl or mono-amino functional compound containing at least one cyclic structural element with a diisocyanate in a stoichiometry effective to yield an intermediate product which is a 1:1 adduct of the mono-hydroxyl or mono-amino functional compound containing at least one cyclic structural element and the diisocyanate and which contains at least one cyclic structural element, a single isocyanate group and a urethane or ureido linkage;
b) reacting the intermediate product with a mono-hydroxyl or mono-amino functional compound containing a single free radical-polymerizable functional group.

Aspect 29: A method of making a compound in accordance with Aspect 1 to 18, comprising the steps of:
a) reacting i) a mono-hydroxyl or mono-amino functional compound containing at least one cyclic structural element, ii) a diisocyanate and iii) a di-hydroxyl, di-amino or mono-hydroxy and mono-amino functional compound containing at least one cyclic structural element in a stoichiometry effective to yield an intermediate product which is a 1:X:Y adduct of the mono-hydroxyl or mono-amino functional compound containing at least one cyclic structural element, the diisocyanate and the di-hydroxyl, di-amino or mono-hydroxy and mono-amino functional compound containing at least one cyclic structural element and which contains at least two cyclic structural elements, a single isocyanate group and two or more urethane or ureido linkages, wherein X is an integer of 1 or more and represents the number of moles of di-hydroxyl, di-amino or mono-hydroxy and mono-amino functional compound containing at least one cyclic structural element incorporated in the adduct per mole of mono-hydroxyl or mono-amino functional compound containing at least one cyclic structural element, and Y=X+1 and represents the number of moles of diisocyanate incorporated in the adduct per mole of mono-hydroxyl or mono-amino functional compound containing at least one cyclic structural element;

b) reacting the intermediate product with a mono-hydroxyl or mono-amino functional compound containing a single free radical-polymerizable functional group.

Aspect 30: A method of making a cured composition according to Aspect 23, comprising curing a curable composition comprised of at least one compound in accordance with any one of Aspects 1-18.

Aspect 31: A method of making a three-dimensional article by using a compound according to any one of Aspects 1 to 18, comprising the steps of:

a) coating a first layer of a composition comprising at least one compound in accordance with any one of Aspects 1-18 onto a surface;
b) curing the first layer to provide a cured first layer;
c) coating a second layer of the composition onto the cured first layer;
d) curing the second layer to provide a cured second layer adhered to the cured first layer; and
e) repeating steps c) and d) a desired number of times to build up the three-dimensional article.

Aspect 32: The method of Aspect 31, wherein the curing steps are performed by exposing the layer of the composition to radiation, preferably UV or EB radiation.

Aspect 33: Use of a compound according to any Aspect 1 to 18 in curable compositions in a coating, an adhesive, a sealant, an ink, a 3D printing resin or a molding resin.

DETAILED DESCRIPTION OF THE INVENTION

Inventive Monofunctional Compounds

The inventive monofunctional compounds may be characterized as corresponding to the following general formula (I):

Q-(R$^1$Z$^1$)$_m$—RZ  (I)

Q is a moiety containing a single free radical-polymerizable functional group, that is, a functional group capable of participating in a curing or polymerization reaction that proceeds via a free radical mechanism. The free radical-polymerizable functional group present in the moiety Q is the sole such functional group present in the compound. In one embodiment, the free radical-polymerizable functional group is an ethylenically unsaturated functional group. Ethylenically unsaturated functional groups suitable for use in the present invention include groups containing at least one carbon-carbon double bond, in particular a carbon-carbon double bond capable of participating in a free radical reaction wherein at least one carbon of the carbon-carbon double bond becomes covalently bonded to an atom, in particular a carbon atom, in a second molecule. Such reactions may result in a polymerization or curing whereby the compound containing the ethylenically unsaturated functional group becomes part of a polymerized matrix or polymeric chain. The carbon-carbon double bond may, for example, be present as part of an α,β-unsaturated carbonyl moiety, e.g., an α,β-unsaturated ester moiety such as an acrylate functional group (H$_2$C=CH—C(=O)O—) or a methacrylate functional group (H$_2$C=C(CH$_3$)—C(=O)O—). A carbon-carbon double bond may also be present in the ethylenically unsaturated functional group in the form of a vinyl group —CH=CH$_2$ (such as an allyl group, —CH$_2$—CH=CH$_2$).

The remainder, if any, of the Q moiety besides the free radical-polymerizable functional group may be any suitable radical or structural element that functions to link the free radical-polymerizable group to an R$^1$ (where m=1 or more) or R (where m=0) in the inventive monofunctional compound. Such remainder of the Q moiety may be of any structure, provided that the free radical-polymerizable functional group remains capable of participating in a free radical curing or polymerization reaction and the remainder of the Q moiety does not adversely interfere with such curing or polymerization. For example, the free radical-polymerizable functional group may be bonded directly to R$^1$ or R or linked to R$^1$ or R through an alkylene, arylene, aralkylene, oxyalkylene or other such linking group. Such bonding or linkage may be to an oxygen or nitrogen atom forming part of a urethane or ureido linkage in R$^1$ or R.

Illustrative examples of moieties suitable for use as Q in the inventive monofunctional compounds include, but are not limited to, alkylene (meth)acrylate moieties having, for example, the structure H$_2$C=C(R$^2$)C(=O)—O—R$^3$—, wherein R$^2$ is H or CH$_3$ and R$^3$ is a straight chain, cyclic or branched alkylene group containing, for example, two to twelve carbon atoms. R$^3$ may be, for example, —CH$_2$CH$_2$—, —CH$_2$CH(CH$_3$)—, —CH$_2$CH$_2$CH$_2$—, —CH$_2$CH$_2$CH$_2$CH$_2$—, cyclohexyl, —CH$_2$—CyHx- (where CyHx=cyclohexane) and the like. In other embodiments, R$^3$ may be —CH$_2$CH$_2$—[OC(=O)C$_5$H$_{10}$]$_n$—, where n=an integer of 1 to 4 (C$_5$H$_{10}$ may be —(CH$_2$)$_5$—, for example). R$^3$ may also be an oligoether moiety (i.e., a moiety containing one or more, e.g., one to six, oxyalkylene units such as oxyethylene and/or oxypropylene) or an oligoester moiety (e.g., a moiety containing one or more ester units such as —OC(=O)(CH$_2$)$_p$—, where p is an integer of 2 or more, e.g., 2-8).

Particular non-limiting examples of suitable Q moieties include H$_2$C=CHC(=O)OCH$_2$CH$_2$—, H$_2$C=CHC(=O)OCH$_2$CH$_2$CH$_2$—, H$_2$C=CHC(=O)OCH$_2$CH(CH$_3$)— and the methacrylate analogues thereof and the like.

In formula (I), m may be 0 or an integer of 1 or more. For example, m may be 1, 2, 3, 4, 5 or more; mixtures of inventive monofunctional compounds having different values of m are contemplated in the present invention.

In embodiments where m=0, the moiety Q is directly bonded to R, which is a urethane/ureido-containing structural unit (that is, a structural unit comprised of at least one urethane and/or ureido group). In one embodiment of the invention, R contains two urethane groups or two ureido groups or one urethane group and one ureido group. A urethane group corresponds to structure —O—C(=O)—NH—, whereas a ureido group corresponds to structure —NH—C(=O)—NH— or —NR—C(=O)—NH—, wherein R can be, for example, a C$_1$-C$_6$ alkyl group. As will be explained subsequently in more detail, a urethane structural unit may be formed by reaction of a hydroxyl group (—OH) with an isocyanate group (OCN—), whereas a ureido structural unit may be formed by reaction of a primary or secondary amino group (—NH$_2$ or —NHR) with an isocyanate group. In certain embodiments of the invention (where m=0), a urethane or ureido group in R functions to link R to the moiety Q. That is, a urethane or ureido group in R is bonded to an atom (e.g., a carbon atom) in Q. In other embodiments, a urethane or ureido group in R is bonded to an atom (e.g., a carbon atom) in Z. According to certain embodiments of the invention, one urethane or ureido group in R links R to Q and a second urethane or ureido group links R to Z. In such embodiments, R may thus correspond to the general structure -T-C(=O)NH—R$^4$—NH—C(=O)-T$^1$-, wherein T and T$^1$ are independently —O—, —NH— or —NR$^5$— and R$^4$ is a linking moiety such as a divalent hydrocarbon radical (which may be, for example, aliphatic, aromatic, alicyclic, aralkyl or the like) and R$^5$ is a substituent other than H such as an alkyl group. In embodiments where a diisocyanate has been employed for the purpose of synthesizing the inventive monofunctional compound, R$^4$ represents the residue of the diisocyanate other than the isocyanate groups (for example, an isophorone residue, where isophorone has been used as the diisocyanate).

Z is a monovalent moiety bonded to R which contains at least one cyclic structural element. Including a cyclic structural element in moiety Z has been found to provide a monofunctional compound which, when cured (polymerized), results in a cured composition having improved mechanical properties, such as higher hardness and stiffness as compared to a cured composition based on a urethane (meth)acrylate that does not contain any cyclic structural elements. In certain embodiments of the invention (where m is an integer of 1 or more), the inventive monofunctional compound also comprises one or more Z$^1$ moieties each containing at least one cyclic structural element.

The cyclic structural element(s) contained in moiety Z and moieties Z$^1$ (if present) may be any cyclic structure including (formed by) atoms selected from the group consisting of carbon, oxygen, nitrogen and sulfur atoms. In embodiments where the inventive monofunctional compound contains a Z$^1$ moiety in addition to the Z moieties, the cyclic structural elements in each of Z and Z$^1$ may be the same as or different from each other. In embodiments where the inventive monofunctional compound contains two or more Z$^1$ moieties, the cyclic structural element(s) in such Z$^1$ moieties may be the same as or different from each other and the same as or different from the cyclic structural element(s) present in Z. Moieties Z and Z$^1$ do not contain any free radical-polymerizable functional groups. In particular aspects of the invention, the cyclic structural element(s) is or are selected from the group consisting of aliphatic hydrocarbon rings (in particular, saturated aliphatic hydrocarbon rings), aromatic hydrocarbon rings, heterocyclic rings and combinations thereof.

Suitable aliphatic hydrocarbon rings include monocyclic aliphatic hydrocarbon rings and polycyclic aliphatic hydrocarbon rings, especially saturated monocyclic aliphatic hydrocarbon rings and saturated polycyclic aliphatic hydrocarbon rings. Monocyclic aliphatic hydrocarbon rings include, but are not limited to, cycloalkane rings such as a cyclopropane ring, a cyclobutane ring, a cyclopentane ring, a cyclohexane ring, a cycloheptane ring or a cyclooctane ring or $C_3$-$C_{10}$ cycloalkane rings generally.

Suitable polycyclic aliphatic hydrocarbon rings include, but are not limited to, bridged rings such as a norbornane ring, a bicyclo[3.2.1]octane ring, a bicyclo[4.3.2]undecane ring, an adamantane ring, a tricyclodecane ring or a tetracyclododecane ring, as well as spiro rings. Suitable aromatic hydrocarbon rings include, but are not limited to, monocyclic aromatic hydrocarbon rings, such as a benzene ring and polycyclic aromatic hydrocarbon rings typified by fused benzene rings such as a naphthalene ring, an anthracene ring, a phenanthrene ring, a fluorene ring, an indene ring or a pyrene ring.

Suitable heterocyclic rings include, but are not limited to, heterocyclic rings including carbon atom(s) and oxygen atom(s); heterocyclic rings including carbon atom(s) and nitrogen atom(s); and heterocyclic rings including carbon atom(s) and sulfur atom(s). More specifically, suitable heterocyclic rings include non-aromatic heterocyclic rings such as an oxirane ring, a tetrahydrofuran ring, a tetrahydropyran ring, a morpholine ring, a chroman ring, an isochroman ring, a tetrahydrothiophene ring, a tetrahydrothiopyran ring, an aziridine ring, a pyrrolidine ring, a piperidine ring, a piperazine ring, an indoline ring, a 2,6-dioxabicyclo[3.3.0]octane ring or a 1,3,5-triazacyclohexane ring; and aromatic heterocyclic rings such as a thiophene ring, a pyrrole ring, a furan ring or a pyridine ring.

The cyclic structural element, including any of the cyclic structural elements above-mentioned, may be unsubstituted (where the atoms forming the cyclic structure and not involved in bonding to R and/or R$^1$ or to a group or groups linking the cyclic structural element to R and/or R$^1$ are not substituted by any substituent other than hydrogen) or substituted (where one or more of the atoms forming the cyclic structure and not involved in bonding to R and/or R$^1$ or to a group or groups linking the cyclic structural element to R and/or R$^1$ are substituted by a substituent other than hydrogen, such as an alkyl group, an aryl group, an alkaryl group, an alkoxy group, a halide or the like, provide that such substituent(s) do not interfere with the ability of the inventive monofunctional compound to be used for its intended purpose in a free radical-curable composition). In embodiments of the invention, the cyclic structural element(s) is or are selected from the group consisting of saturated, unsubstituted bicyclic and tricyclic hydrocarbon radicals. The cyclic structural element(s) may, for example, be selected from the group consisting of a tricyclo[5.2.1.0$^{2,6}$]decane radical, a tricyclo[3.3.1.1$^{3,7}$]decane radical and a bicyclo[2.2.1]heptane radical.

Methods of Making Inventive Monofunctional Compounds

The inventive monofunctional compounds may be conveniently prepared by reacting diisocyanates, mono-hydroxyl or mono-amino functional compounds containing a single free radical-polymerizable functional group per molecule and mono-hydroxyl or mono-amino functional compounds containing at least one cyclic structural element per molecule. In embodiments where m in Formula (I) is an integer of 1 or more, di-hydroxyl, di-amino or monohydroxy and mono-amino functional compounds containing at least one cyclic structural element per molecule are also utilized as reactants.

The diisocyanate is a compound containing two isocyanate groups per molecule. As used herein, the term "isocyanate groups" includes both free isocyanate groups (—NCO) as well as blocked isocyanate groups. A single diisocyanate or a combination of different diisocyanates may be employed. Diisocyanates suitable for use herein may be selected from, but are not limited to, known or common compounds containing two isocyanate groups per molecule. Such compounds include diisocyanates devoid of cyclic structural elements in the molecule (including any of the cyclic structural elements mentioned above in connection with the moieties Q, R, R$^1$, Z and Z$^1$) as well as diisocyanates containing one or more cyclic structural elements in the molecule. The diisocyanates devoid of cyclic structural elements in the molecule are exemplified by diisocyanates such as 1,6-hexane diisocyanate, 2,2,4-trimethylhexamethylene diisocyanate, 1,5-diisocyanato-2-methylpentane, 1,6-diisocyanato-2,4,4-trimethylhexane and 2,4,4-trimethylhexamethylene diisocyanate. The diisocyanates containing a cyclic structural element in the molecule are exemplified by aromatic diisocyanates such as xylylene diisocyanates, phenylene diisocyanates, toluene diisocyanates and diphenylmethane diisocyanates and alicyclic diisocyanates such as cyclohexane diisocyanates, methylcyclohexane diisocyanates, ethylcyclohexane diisocyanates, propylcyclohexane diisocyanates, methyldiethylcyclohexane diisocyanates, dicyclohexylmethane diisocyanates, bis(isocyanatomethyl) cyclohexanes and diisocyanates prepared by hydrogenation of aromatic diisocyanates and isophorone diisocyanate, as well as combinations of such diisocyanates.

Mono-hydroxyl or mono-amino functional compounds containing a single free radical-polymerizable functional group per molecule suitable for use in preparing the inventive monofunctional compound are selected based on the type of free radical-polymerizable functional group desired in the final monofunctional inventive compound. Such compounds include a single hydroxyl group (—OH) or a single amino group (primary or secondary) that is capable of reacting with an isocyanate group to form a urethane (in the case of hydroxyl) or ureido (in the case of amino) linkage. In one embodiment, the free radical-polymerizable functional group is an ethylenically unsaturated functional group. As previously mentioned, ethylenically unsaturated functional groups suitable for use in the present invention include groups containing at least one carbon-carbon double bond, in particular a carbon-carbon double bond capable of participating in a free radical reaction wherein at least one carbon of the carbon-carbon double bond becomes covalently bonded to an atom, in particular a carbon atom, in a second molecule. Such reactions may result in a polymerization or curing whereby the compound containing the ethylenically unsaturated functional group becomes part of a polymerized matrix or polymeric chain. The carbon-carbon double bond may, for example, be present as part of an $\alpha,\beta$-unsaturated carbonyl moiety, e.g., an $\alpha,\beta$-unsaturated ester moiety such as an acrylate functional group ($H_2C=CH-C(=O)O-$) or a methacrylate functional group ($H_2C=C(CH_3)-C(=O)O-$). A carbon-carbon double bond may also be present in the ethylenically unsaturated functional group in the form of a vinyl group —CH=CH$_2$ (such as an allyl group, —CH$_2$—CH=CH$_2$).

Illustrative examples of compounds suitable for use for the purpose of introducing the moiety Q in the inventive monofunctional compounds include, but are not limited to, hydroxyl- and aminoalkyl (meth)acrylates having, for example, the structure $H_2C=C(R^2)C(=O)-O-R^3-T-H$, wherein $R^2$ is H or $CH_3$, $R^3$ is a straight chain, cyclic or branched alkylene group containing, for example, two to twelve carbon atoms and T is —O— (oxygen) or —NR$^5$— (where R$^5$ is H or a substituent such as an alkyl group). $R^3$ may be, for example, —CH$_2$CH$_2$—, —CH$_2$CH(CH$_3$)—, —CH$_2$CH$_2$CH$_2$—, —CH$_2$CH$_2$CH$_2$CH$_2$—, cyclohexyl, —CH$_2$—CyHx-CH$_2$— (where CyHx is a cyclohexane ring) and the like. In other embodiments, $R^3$ may be an oligoether moiety, such as an oligooxyalkylene moiety (e.g., —(CH$_2$CH$_2$O)$_n$CH$_2$CH$_2$—, where n is an integer of 1 or more, e.g., 1-6). $R^3$ may also be an oligoester moiety, such as —CH$_2$CH$_2$—[OC(=O)C$_5$H$_{10}$]$_n$—, where n=an integer of 1 to 4 and C$_5$H$_{10}$ is —CH$_2$CH$_2$CH$_2$CH$_2$CH$_2$—.

Particular non-limiting examples of suitable mono-hydroxyl or mono-amino functional compounds containing a single free radical-polymerizable functional group per molecule include $H_2C=CHC(=O)OCH_2CH_2—OH$, $H_2C=C(CH_3)C(=O)OCH_2CH_2—OH$, $H_2C=CHC(=O)OCH_2CH_2CH_2—OH$, $H_2C=C(CH_3)C(=O)OCH_2CH_2CH_2—OH$, $H_2C=CHC(=O)OCH_2CH(CH_3)—OH$, $H_2C=C(CH_3)C(=O)OCH_2CH(CH_3)—OH$, $H_2C=CHC(=O)O(CH_2CH_2O)_nCH_2CH_2—OH$ (wherein n=an integer of 1 or more, e.g., 1-6), $H_2C=C(CH_3)C(=O)O(CH_2CH_2O)_nCH_2CH_2—OH$ (wherein n=an integer of 1 or more, e.g., 1-6), 2-hydroxy-3-phenoxypropyl (meth)acrylate, cyclohexanedimethanol mono(meth)acrylate, cyclohexanediol mono(meth)acrylate, hydroxybutyl(meth)acrylates, hydroxypentyl(meth)acrylates, 3-hydroxy-2,2-dimethylpropyl(meth)acrylate, hydroxyheptyl(meth) acrylates, hydroxyoctyl(meth)acrylates, hydroxynonyl (meth)acrylates, caprolactone-capped hydroxyalkyl (meth) acrylates and the like (including the amino analogues, wherein —OH is replaced by —NH$_2$ or —NHR, with R being an alkyl group such as a t-butyl group, as in t-butylaminoethyl methacrylate), N-vinyl formamide adducts of hydroxyalkyl (meth)acrylates such as hydroxyethyl (meth) acrylate, hydroxypropyl(meth)acrylate and hydroxybutyl (meth)acrylate, which generally have the structure HC(=O)N(CHR=CH$_2$)CH$_2$CH$_2$C(=O)OR'OH (R=H or CH$_3$, R'=alkylene, e.g. ethylene, propylene, butylene) as well as unsaturated alcohols and amines and hydroxy- and amino-substituted vinyl aromatic compounds such as allyl alcohol and hydroxystyrenes.

Mono-hydroxyl or mono-amino functional compounds containing at least one cyclic structural element per molecule are utilized as a source of the moiety Z in the inventive monofunctional compound, wherein Z is a monovalent moiety bonded to R which contains at least one cyclic structural element. Suitable cyclic structural elements have been previously discussed in detail and any compound containing such a cyclic structural element and a single hydroxyl group (—OH) or a single amino group (primary or secondary) that is capable of reacting with an isocyanate group to form a urethane (in the case of hydroxyl) or ureido (in the case of amino) linkage may be utilized in synthesizing the inventive monofunctional compound.

The hydroxyl or amino group may be directly substituted on a cyclic structural element (i.e., the oxygen or nitrogen atom is bonded directly to an atom, such as a carbon atom, that is part of the cyclic structure) or may be linked to a cyclic structural element through a non-cyclic moiety such as an alkylene group. Suitable mono-hydroxyl or mono-amino functional compounds containing at least one cyclic structural element per molecule include, but are not limited to, tricyclodecanemethanol, cyclohexanol, cyclohexanemethanol, phenol and other phenolic compounds, monohydroxy-naphthalenes, monohydroxy-anthracenes, monohydroxy-biphenyls and the amino-substituted analogues thereof.

Where it is desired to introduce one or more Z$^1$ moieties into the inventive monofunctional compound, at least one di-hydroxyl, di-amino or mono-hydroxy and mono-amino functional compound containing at least one cyclic structural element per molecule is also utilized as a reactant in combination with the abovementioned other types of reactants. Such compounds are characterized by containing two hydroxyl groups, two amino (primary or secondary) groups or one hydroxyl group and one amino group per molecule, in addition to one or more cyclic structural elements. The cyclic structural elements may be any of the types previously described in detail.

Such compounds include bisphenols, alkylene oxide (e.g., ethylene oxide, propylene oxide) adducts thereof and hydrogenated derivatives thereof such as bisphenol-A and alkylene oxide adducts thereof, bisphenol-F and alkylene oxide adducts thereof, hydrogenated bisphenol-A and alkylene oxide adducts thereof, hydrogenated bisphenol-F and alkylene oxide adducts thereof, cyclohexanediols and alkylene oxide adducts thereof, cyclohexanedimethanols and alkylene oxide adducts thereof, tricyclodecanedimethanols (including all isomers thereof such as 3,8-bis(hydroxymethyl)tricyclo[5.2.1.0$^{2,6}$]decane, 4,8-bis(hydroxymethyl)tricyclo[5.2.1.0$^{2,6}$]decane, 3,9-bis(hydroxymethyl)tricyclo[5.2.1.0$^{2,6}$]decane and 4,9-bis(hydroxymethyl)tricyclo[5.2.1.0$^{2,6}$]decane and mixtures thereof) and alkylene oxide adducts thereof, tricyclodecanediethanols and alkylene oxide adducts thereof, xylylene glycols and alkylene oxide adducts thereof, dihydroxybenzenes and alkylene oxide adducts thereof, dihydroxynaphthalenes and alkylene oxide adducts thereof, dihydroxyanthracenes and alkylene oxide adducts thereof, dihydroxybiphenyls and alkylene oxide adducts thereof and the like and the amino-functionalized analogues thereof.

In various embodiments of the invention, the abovementioned reactants are combined and reacted with each other in a sequential, stepwise manner using controlled stoichiometries so as to obtain the target inventive monofunctional compound in high yield/purity. For example, the synthesis of an inventive monofunctional compound may be carried out using any one of the following general methods

| Method 1: | Step 1: A + B → A-B |
| | Step 2: A-B + C → A-B-C |
| Method 2: | Step 1: B + C → B-C |
| | Step 2: A + B-C → A-B-C |
| Method 3: | Step 1: A + B + D → A(B-D)$_m$ |
| | Step 2: A(B-D)$_m$B + C → A(B-D)$_m$B-C |
| Method 4: | Step 1: D + B + C → (B-D)$_m$B-C |
| | Step 2: A + (B-D)$_m$B-C → A(B-D)$_m$B-C |

A=mono-hydroxyl or mono-amino functional compound containing a single free radical-polymerizable functional group per molecule
B=diisocyanate
C=mono-hydroxyl or mono-amino functional compound containing at least one cyclic structural element per molecule
D=di-hydroxyl, di-amino or mono-hydroxy and mono-amino functional compound containing at least one cyclic structural element per molecule Methods 1 and 2 may be used for embodiments wherein m in Formula (I) is 0, while Methods 3 and 4 may be used where the value of m is 1 or greater. To the extent that each step of each approach relies on a urethane- or ureido-forming reaction between an isocyanate group and a hydroxyl group or an amino group, such reaction may be accelerated by the use of catalyst (e.g., a tin catalyst) and/or heating. While an inert solvent may be present to function as a reaction medium, in other embodiments the reactions are carried out neat (without solvent). A further explanation of exemplary synthetic procedures which may be used is provided as follows.

Method 1 may involve the steps of:
a) reacting a mono-hydroxyl or mono-amino functional compound containing a single free radical-polymerizable functional group with a diisocyanate in a stoichiometry effective to yield an intermediate product which is a 1:1 adduct of the mono-hydroxyl or mono-amino functional compound containing a single free radical-polymerizable functional group and the diisocyanate and which contains a single free radical-polymerizable functional group, a single isocyanate group and a urethane or ureido linkage;
b) reacting the intermediate product with a mono-hydroxyl or mono-amino functional compound containing at least one cyclic structural element.

Method 2 may involve the steps of:
a) reacting i) a mono-hydroxyl or mono-amino functional compound containing a single free radical-polymerizable functional group, ii) a diisocyanate and iii) a di-hydroxyl, di-amino or mono-hydroxy and mono-amino functional compound containing at least one cyclic structural element in a stoichiometry effective to yield an intermediate product which is a 1:X:Y adduct of the mono-hydroxyl or mono-amino functional compound containing a single free radical-polymerizable functional group, the diisocyanate and the di-hydroxyl, di-amino or mono-hydroxy and mono-amino functional compound containing at least one cyclic structural element and which contains a single free radical-polymerizable functional group, a single isocyanate group and two or more urethane or ureido linkages, wherein X is an integer of 1 or more and represents the number of moles of di-hydroxyl, di-amino or mono-hydroxy and mono-amino functional compound containing at least one cyclic structural element incorporated in the adduct per mole of mono-hydroxyl or mono-amino functional compound containing a single free radical-polymerizable functional group and Y=X+1 and represents the number of moles of diisocyanate incorporated in the adduct per mole of mono-hydroxyl or mono-amino functional compound containing a single free radical-polymerizable functional group;
b) reacting the intermediate product with a mono-hydroxyl or mono-amino functional compound containing at least one cyclic structural element.

Method 3 may involve the following steps:
a) reacting a mono-hydroxyl or mono-amino functional compound containing at least one cyclic structural element with a diisocyanate in a stoichiometry effective to yield an intermediate product which is a 1:1 adduct of the mono-hydroxyl or mono-amino functional compound containing at least one cyclic structural element and the diisocyanate and which contains at least one cyclic structural element, a single isocyanate group and a urethane or ureido linkage;
b) reacting the intermediate product with a mono-hydroxyl or mono-amino functional compound containing a single free radical-polymerizable functional group.

Method 4 may involve the following steps:
a) reacting i) a mono-hydroxyl or mono-amino functional compound containing at least one cyclic structural element, ii) a diisocyanate and iii) a di-hydroxyl, di-amino or mono-hydroxy and mono-amino functional compound containing at least one cyclic structural element in a stoichiometry effective to yield an intermediate product which is a 1:X:Y adduct of the mono-hydroxyl or mono-amino functional compound containing at least one cyclic structural element, the diisocyanate and the di-hydroxyl, di-amino or mono-hydroxy and mono-amino functional compound containing at least one cyclic structural element and which contains at least two cyclic structural elements, a single isocyanate group and two or more urethane or ureido linkages, wherein X is an integer of 1 or more and represents the number of moles of di-hydroxyl, di-amino or mono-hydroxy and mono-amino functional compound containing at least one cyclic structural element incorporated in the adduct per mole of mono-hydroxyl or mono-amino functional compound containing at least one cyclic structural element and Y=X+1 and represents the number of moles of diisocyanate incorporated in the adduct per mole of mono-hydroxyl or mono-amino functional compound containing at least one cyclic structural element;

b) reacting the intermediate product with a mono-hydroxyl or mono-amino functional compound containing a single free radical-polymerizable functional group.

If so desired, the reaction product obtained following the procedures of Methods 1-4 may be subjected to one or more further processing or purification steps such as, for example, solvent removal, decolorization, removal/separation of unreacted reactants and/or byproducts (by techniques such as distillation, extraction, filtration and the like) and so forth.

Uses for the Inventive Monofunctional Compounds

The inventive monofunctional compounds described herein may be suitably used as components of compositions that are to be subjected to curing by means of free radical polymerization or other types of polymerization (e.g., cationic polymerization). In various embodiments, one or more inventive monofunctional compounds are employed in combination with one or more other types of compounds that are also able to be cured by free radical polymerization or other such means (e.g., conventional or otherwise known (meth) acrylates).

End use applications for such compositions include, but are not limited to, inks, coatings, adhesives, 3D printing resins, molding resins, sealants and the like. For example, one or more inventive monofunctional compounds in accordance with the invention may be utilized at levels of 1-20% by weight in a coating or ink formulation, both to help reduce shrinkage of the coating or ink when cured but also to improve the adhesive properties of such formulations. The inventive monofunctional compound could also be used at a 1-50% by weight level in a shrink/thermoformable ink formulation to help improve the adhesion and conformability characteristics of such formulations. In yet another application, the inventive monofunctional compound could be used as a main ingredient (e.g., 50-90% by weight) of a 3D printing resin formulation to deliver thermoplastic-like properties to that formulation when cured. The inventive monofunctional compound could also be employed as a main ingredient (e.g., at a 50-100% by weight level) in an adhesive formulation, which is useful, for example as a UV-curable laminating adhesive or as a UV-curable hotmelt adhesive.

Cured compositions prepared from curable compositions comprised of one or more inventive monofunctional compounds as described herein may be used, for example, in three-dimensional articles (wherein the three-dimensional article may consist essentially of or consist of the cured composition), coated articles (wherein a substrate is coated with one or more layers of the cured composition), laminated or adhered articles (wherein a first component of the article is laminated or adhered to a second component by means of the cured composition) or printed articles (wherein graphics or the like are imprinted on a substrate, such as a paper, plastic or metal substrate, using the cured composition).

Curing of compositions containing one or more inventive monofunctional compounds in accordance with the present invention may be carried out by any suitable method, such as free radical and/or cationic polymerization. One or more initiators, such as a free radical initiator (e.g., photoinitiator, peroxide initiator) may be present in the curable composition. Prior to curing, the composition may be applied to a substrate surface in any known conventional manner, for example, by spraying, knife coating, roller coating, casting, drum coating, dipping and the like and combinations thereof. Indirect application using a transfer process may also be used. A substrate may be any commercially relevant substrate, such as a high surface energy substrate or a low surface energy substrate, such as a metal substrate or plastic substrate, respectively. The substrates may comprise metal, paper, cardboard, glass, thermoplastics such as polyolefins, polycarbonate, acrylonitrile butadiene styrene (ABS) and blends thereof, composites, wood, leather and combinations thereof. When used as an adhesive, the composition may be placed between two substrates and then cured, the cured composition thereby bonding the substrates together.

Curing may be accelerated or facilitated by supplying energy to the composition, such as by heating the composition and/or by exposing the composition to a radiation source, such as visible or UV light, infrared radiation and/or electron beam radiation. Thus, the cured composition may be deemed the reaction product of the curable composition, formed by curing.

A plurality of layers of a composition in accordance with the present invention may be applied to a substrate surface; the plurality of layers may be simultaneously cured (by exposure to a single dose of radiation, for example) or each layer may be successively cured before application of an additional layer of the composition.

The inventive monofunctional compounds described herein are especially useful in 3D printing resin formulations, that is, compositions intended for use in manufacturing three dimensional articles using 3D printing techniques. Such three dimensional articles may be free-standing/self-supporting and may consist essentially of or consist of a composition comprised of one or more inventive monofunctional compounds and possibly one or more additional free radical-curable monomers and/or oligomers as well as other components such as initiators, fillers and the like that has been cured. The three-dimensional article may also be a composite, comprising at least one component consisting essentially of or consisting of a cured composition as previously mentioned as well as at least one additional component comprised of one or more materials other than such a cured composition (for example, a metal component or a thermoplastic component). The presence of the inventive monofunctional compound(s) helps to reduce the amount of shrinkage exhibited by the composition when cured, as compared to analogous compositions where the inventive monofunctional compound(s) is or are replaced by conventional polyfunctional urethane (meth)acrylates (containing two or more free radical-polymerizable functional groups per molecule).

A method of making a three-dimensional article using one or more inventive monofunctional compounds in accordance with the present invention may comprise the steps of:
a) coating a first layer of a composition comprising at least one inventive monofunctional compound in accordance with the present invention onto a surface;
b) curing the first layer to provide a cured first layer;
c) coating a second layer of the composition onto the cured first layer;
d) curing the second layer to provide a cured second layer adhered to the cured first layer; and
e) repeating steps c) and d) a desired number of times to build up the three-dimensional article.

Although the curing steps may be carried out by any suitable means, which will in some cases be dependent upon the components present in the composition, in certain embodiments of the invention the curing is accomplished by exposing the layer to be cured to an effective amount of radiation (e.g., electron beam radiation, UV radiation, visible light, etc.).

Accordingly, in various embodiments, the present invention provides a process comprising the steps of:

a) coating a first layer of a composition comprising at least one inventive monofunctional compound in accordance with the present invention and in liquid form onto a surface;
b) exposing the first layer imagewise to actinic radiation to form a first exposed imaged cross-section, wherein the radiation is of sufficient intensity and duration to cause at least partial curing (e.g., at least 80% or at least 90% curing) of the layer in the exposed areas;
c) coating an additional layer of the composition onto the previously exposed imaged cross-section;
d) exposing the additional layer imagewise to actinic radiation to form an additional imaged cross-section, wherein the radiation is of sufficient intensity and duration to cause at least partial curing (e.g., at least 80% or at least 90% curing) of the additional layer in the exposed areas and to cause adhesion of the additional layer to the previously exposed imaged cross-section;
e) repeating steps c) and d) a desired number of times to build up the three-dimensional article.

Compositions Based on the Inventive Monofunctional Compounds

As previously mentioned, the inventive monofunctional compounds of the invention may be formulated with one or more other components, in particular initiators and/or other types of free radical-curable compounds, to provide curable compositions useful as inks, molding resins, 3D printing resins, coatings, sealants and adhesives.

Ethylenically unsaturated compounds suitable for use in combination with the inventive monofunctional compound(s) of the present invention include compounds containing at least one carbon-carbon double bond, in particular a carbon-carbon double bond capable of participating in a free radical reaction wherein at least one carbon of the carbon-carbon double bond becomes covalently bonded to an atom, in particular a carbon atom, in a second molecule. Such reactions may result in a polymerization or curing whereby the ethylenically unsaturated compound becomes part of a polymerized matrix or polymeric chain. In various embodiments of the invention, the additional ethylenically unsaturated compound(s) may contain one, two, three, four, five or more carbon-carbon double bonds per molecule. Combinations of multiple ethylenically unsaturated compounds containing different numbers of carbon-carbon double bonds may be utilized in the compositions of the present invention. The carbon-carbon double bond may be present as part of an α,β-unsaturated carbonyl moiety, e.g., an α,β-unsaturated ester moiety such as an acrylate functional group or a methacrylate functional group. A carbon-carbon double bond may also be present in the additional ethylenically unsaturated compound in the form of a vinyl group —CH=CH$_2$ (such as an allyl group, —CH$_2$—CH=CH$_2$). Two or more different types of functional groups containing carbon-carbon double bonds may be present in the additional ethylenically unsaturated compound. For example, the ethylenically unsaturated compound may contain two or more functional groups selected from the group consisting of vinyl groups (including allyl groups), acrylate groups, methacrylate groups and combinations thereof.

The compositions of the present invention may, in various embodiments, contain one or more (meth)acrylate functional compounds capable of undergoing free radical polymerization (curing), in addition to one or more inventive monofunctional compounds as described herein. As used herein, the term "(meth)acrylate" refers to methacrylate (—O—C(=O)—C(CH$_3$)=CH$_2$) as well as acrylate (—O—C(=O)—CH=CH$_2$) functional groups. Suitable free radical-curable (meth)acrylates include compounds containing one, two, three, four or more (meth)acrylate functional groups per molecule; the free radical-curable (meth)acrylates may be oligomers or monomers. The at least one additional ethylenically unsaturated monomer or oligomer may include, for example, at least one compound selected from the group consisting of cyclic, linear and branched mono-, di- and tri-(meth)acrylate-functionalized monomers and oligomers.

The amount of additional free radical-curable compounds relative to the amount of inventive monofunctional compound is not believed to be critical and may be selected or controlled as may be appropriate or desired to attain certain properties in the composition or the cured resin obtained therefrom.

Suitable free radical-curable (meth)acrylate oligomers include, for example, polyester (meth)acrylates, epoxy (meth)acrylates, polyether (meth)acrylates, polyurethane (meth)acrylates, acrylic (meth)acrylate oligomers, epoxy-functional (meth)acrylate oligomers and combinations thereof. Such oligomers may be selected and used in combination with the inventive monofunctional compound in order to enhance the flexibility, strength and/or modulus, among other attributes, of a cured composition containing the inventive monofunctional compound.

Exemplary polyester (meth)acrylates include the reaction products of acrylic or methacrylic acid or mixtures thereof with hydroxyl group-terminated polyester polyols. The reaction process may be conducted such that a significant concentration of residual hydroxyl groups remain in the polyester (meth)acrylate or may be conducted such that all or essentially all of the hydroxyl groups of the polyester polyol have been (meth)acrylated. The polyester polyols can be made by polycondensation reactions of polyhydroxyl functional components (in particular, diols) and polycarboxylic acid functional compounds (in particular, dicarboxylic acids and anhydrides). The polyhydroxyl functional and polycarboxylic acid functional components can each have linear, branched, cycloaliphatic or aromatic structures and can be used individually or as mixtures.

Examples of suitable epoxy (meth)acrylates include the reaction products of acrylic or methacrylic acid or mixtures thereof with glycidyl ethers or esters.

Suitable polyether (meth)acrylates include, but are not limited to, the condensation reaction products of acrylic or methacrylic acid or mixtures thereof with polyetherols which are polyether polyols. Suitable polyetherols can be linear or branched substances containing ether bonds and terminal hydroxyl groups. Polyetherols can be prepared by ring opening polymerization of cyclic ethers such as tetrahydrofuran or alkylene oxides with a starter molecule. Suitable starter molecules include water, hydroxyl functional materials, polyester polyols and amines.

Polyurethane (meth)acrylates (sometimes also referred to as "urethane (meth)acrylates") capable of being used in the compositions of the present invention include urethanes based on aliphatic and/or aromatic polyester polyols and polyether polyols and aliphatic and/or aromatic polyester diisocyanates and polyether diisocyanates capped with (meth)acrylate end-groups. Suitable polyurethane (meth)acrylates include, for example, aliphatic polyester-based urethane diacrylate oligomers, aliphatic polyether-based urethane diacrylate oligomers, as well as aliphatic polyester/polyether-based urethane diacrylate oligomers.

In various embodiments, the polyurethane (meth)acrylates may be prepared by reacting aliphatic and/or aromatic diisocyanates with OH group terminated polyester polyols (including aromatic, aliphatic and mixed aliphatic/aromatic polyester polyols), polyether polyols, polycarbonate polyols, polycaprolactone polyols, polydimethysiloxane polyols or polybutadiene polyols or combinations thereof to form isocyanate-functionalized oligomers which are then reacted with hydroxyl-functionalized (meth)acrylates such as hydroxyethyl acrylate or hydroxyethyl methacrylate to provide terminal (meth)acrylate groups. For example, the polyurethane (meth)acrylates may contain two, three, four or more (meth)acrylate functional groups per molecule.

One or more urethane diacrylates are employed in certain embodiments of the invention. For example, the composition may comprise (in addition to the inventive monofunctional compound) at least one urethane diacrylate comprising a difunctional aromatic urethane acrylate oligomer, a difunctional aliphatic urethane acrylate oligomer and combinations thereof. In certain embodiments, a difunctional aromatic urethane acrylate oligomer, such as that available from Sartomer USA, LLC (Exton, Pa.) under the trade name CN9782, may be used as the at least one urethane diacrylate. In other embodiments, a difunctional aliphatic urethane acrylate oligomer, such as that available from Sartomer USA, LLC under the trade name CN9023 may be used as the at least one urethane diacrylate. CN9782, CN9023, CN978, CN965, CN9031, CN8881 and CN8886, all available from Sartomer USA, LLC, may all be advantageously employed as urethane diacrylates in the compositions of the present invention.

Suitable acrylic (meth)acrylate oligomers (sometimes also referred to in the art as "acrylic oligomers") include oligomers which may be described as substances having an oligomeric acrylic backbone which is functionalized with one or (meth)acrylate groups (which may be at a terminus of the oligomer or pendant to the acrylic backbone). The acrylic backbone may be a homopolymer, random copolymer or block copolymer comprised of repeating units of acrylic monomers. The acrylic monomers may be any monomeric (meth)acrylate such as $C_1$-$C_6$ alkyl (meth)acrylates as well as functionalized (meth)acrylates such as (meth)acrylates bearing hydroxyl, carboxylic acid and/or epoxy groups. Acrylic (meth)acrylate oligomers may be prepared using any procedures known in the art such as oligomerizing monomers, at least a portion of which are functionalized with hydroxyl, carboxylic acid and/or epoxy groups (e.g., hydroxyalkyl(meth)acrylates, (meth)acrylic acid, glycidyl (meth)acrylate) to obtain a functionalized oligomer intermediate, which is then reacted with one or more (meth)acrylate-containing reactants to introduce the desired (meth)acrylate functional groups. Suitable acrylic (meth)acrylate oligomers are commercially available from Sartomer USA, LLC under products designated as CN820, CN821, CN822 and CN823, for example.

Free radical-curable monomers suitable for use in the present invention include the following types of monomers (wherein "functional" refers to the number of (meth)acrylate functional groups per molecule, e.g., monofunctional=one (meth)acrylate group per molecule, difunctional=two (meth) acrylate groups per molecule):
i) cyclic monofunctional (meth)acrylate monomers, such as isobornyl (meth)acrylate, cyclohexyl (meth)acrylate, 4-tert-butyl cyclohexyl (meth)acrylate and alkoxylated analogues thereof;
ii) linear and branched monofunctional (meth)acrylate monomers, such as isodecyl (meth)acrylate, ethoxyethyl (meth)acrylate, polyethylene mono (meth) acrylates, neopentyl glycol (meth)acrylates and alkoxylated analogues thereof;
iii) cyclic difunctional (meth)acrylate monomers, such as tricyclodecane dimethanol di(meth)acrylate, cyclohexane dimethanol di(meth)acrylate and alkoxylated analogues thereof;
iv) linear difunctional (meth)acrylate monomers, such as polyethylene di(meth)acrylates, neopentyl glycol di(meth)acrylates and alkoxylated analogues thereof; and
v) trifunctional (meth)acrylate monomers, such as triallyl isocyanurate tri(meth)acrylates, trimethylol tri(meth) acrylates and alkoxylated analogues thereof.

Such monomers may be used to reduce the viscosity of the compositions of the present invention and adjust the flexibility, strength and/or modulus, among other properties, of finished articles obtained by curing the compositions.

Illustrative examples of suitable free radical-curable monomers include 1,3-butylene glycol di(meth)acrylate, butanediol di(meth)acrylate, 1,6-hexanediol di(meth)acrylate, alkoxylated hexanediol di(meth)acrylate, alkoxylated aliphatic di(meth)acrylate, alkoxylated neopentyl glycol di(meth)acrylate, dodecyl di(meth) acrylate cyclohexane dimethanol di(meth)acrylate, diethylene glycol di(meth) acrylate, dipropylene glycol di(meth)acrylate, n-alkane, di(meth)acrylate, polyether di(meth) acrylates, ethoxylated bisphenol A di(meth)acrylate, ethylene glycol di(meth)acrylate, neopentyl glycol di(meth)acrylate, polyester di(meth) acrylate, polyethylene glycol di(meth)acrylate, polypropylene glycol di(meth)acrylate, propoxylated neopentyl glycol diacrylate, tricyclodecane dimethanol diacrylate, triethylene glycol di(meth)acrylate, tetraethylene glycol di(meth)acrylate tripropylene glycol di(meth)acrylate, ditrimethylolpropane tetra(meth)acrylate, dipentaerythritol penta(meth)acrylate, ethoxylated pentaerythritol tetra(meth)acrylate, dipentaerythritol penta(meth)acrylate, dipentaerythritol penta(meth)acrylate, penta(meth)acrylate ester, pentaerythritol tetra(meth)acrylate, ethoxylated trimethylolpropane tri (meth)acrylate, alkoxylated trimethylolpropane tri(meth) acrylate, highly propoxylated glyceryl tri(meth)acrylate, trimethylolpropane tri(meth)acrylate, trimethylolpropane tri (meth)acrylate, pentaerythritol tri(meth)acrylate, propoxylated glyceryl tri(meth)acrylate, propoxylated trimethylolpropane tri(meth)acrylate, trimethylolpropane trimethacrylate, tris (2-hydroxy ethyl) isocyanurate tri (meth)acrylate, 2(2-ethoxyethoxy) ethyl (meth)acrylate, 2-phenoxyethyl (meth)acrylate, 3,3,5-trimethylcyclohexyl (meth)acrylate, alkoxylated lauryl (meth)acrylate, alkoxylated phenol (meth)acrylate, alkoxylated tetrahydrofurfuryl (meth)acrylate, caprolactone (meth)acrylate, cyclic trimethylolpropane formal (meth)acrylate, cycloaliphatic acrylate monomer, dicyclopentadienyl (meth)acrylate, diethylene glycol methyl ether (meth)acrylate, ethoxylated (4) nonyl phenol (meth)acrylate, ethoxylated nonyl phenol (meth) acrylate, isobornyl (meth)acrylate, isodecyl (meth)acrylate, isooctyl (meth)acrylate, lauryl (meth)acrylate, methoxy polyethylene glycol (meth)acrylate, octyldecyl (meth)acrylate, stearyl (meth)acrylate, tetrahydrofurfuryl (meth) acrylate, tridecyl (meth)acrylate, and/or triethylene glycol ethyl ether (meth)acrylate, t-butyl cyclohexyl (meth)acrylate, alkyl (meth)acrylate, dicyclopentadiene di(meth)acrylate, alkoxylated nonylphenol (meth)acrylate, phenoxyethanol (meth)acrylate, octyl (meth)acrylate, decyl (meth)acrylate, dodecyl (meth)acrylate, tetradecyl (meth)acrylate, tridecyl (meth)acrylate, cetyl (meth)acrylate, hexadecyl (meth)acrylate, behenyl (meth)acrylate, diethylene glycol ethyl ether (meth)acrylate, diethylene glycol butyl ether (meth)acrylate, triethylene glycol methyl ether (meth)acrylate, dodecanediol di (meth)acrylate, dodecane di (meth)acrylate, dipentaerythritol penta/hexa(meth)acrylate, pentaerythritol tetra(meth) acrylate, ethoxylated pentaerythritol tetra(meth)acrylate, ethoxylated trimethylolpropane tri(meth)acrylate, trimethylolpropane tri(meth)acrylate, di-trimethylolpropane tetra(meth)acrylate, propoxylated glyceryl tri(meth)acrylate, pentaerythritol tri(meth)acrylate, propoxylated glyceryl tri (meth)acrylate, propoxylated trimethylolpropane tri(meth) acrylate, trimethylolpropane tri(meth)acrylate and tris (2-hydroxy ethyl) isocyanurate tri(meth)acrylate and combinations thereof.

Particularly advantageous types of free radical-curable compounds which may be used in combination with the inventive monofunctional urethanes include, but are not limited to, urethane (meth)acrylates, polyester (meth)acrylates, acrylic (meth)acrylate oligomers, epoxy-functional oligomers, cyclic monofunctional monomers, linear and branched monofunctional monomers, cyclic difunctional monomers, trifunctional monomers and combinations thereof.

In certain embodiments of the invention, the curable composition may contain one or more solvents, in particular one or more organic solvents, which may be non-reactive organic solvents. In various embodiments, the solvent(s) may be relatively volatile, e.g., solvents having a boiling point at atmospheric pressure of not more than 150° C. In other embodiments, the solvent(s) may have a boiling point at atmospheric pressure of at least 40° C.

The solvent(s) may be selected so as to be capable of solubilizing one or more components of the composition and/or adjusting the viscosity or other rheological properties of the composition.

However, the curable compositions of the present invention may alternatively be formulated so as to contain little or no non-reactive solvent, e.g., less than 10% or less than 5% or even 0% non-reactive solvent, based on the total weight of the composition. Such solvent-less or low-solvent compositions may be formulated using various components, including for example low viscosity reactive diluents and/or water, which are selected so as to render the composition sufficiently low in viscosity, even without solvent being present, that the composition can be easily applied at a suitable application temperature to a substrate surface so as to form a relatively thin, uniform layer.

Suitable solvents may include, for example, organic solvents such as: ketones (both acyclic ketones and cyclic ketones) such as acetone, methyl ethyl ketone, iso-butyl ethyl ketone and cyclopentanone; esters such as ethyl acetate, butyl acetate, ethylene glycol methyl ether acetate, ethylene glycol monoethyl ether acetate, ethylene glycol monobutyl ether acetate and propylene glycol methyl ether acetate; carbonates such as dimethyl carbonate, propylene glycol carbonate and ethylene glycol carbonate; alcohols such as ethoxyethanol, methoxyethanol, 1-methoxy-2-propanol, methyl alcohol, ethyl alcohol, n-propyl alcohol, butyl alcohol, isopropyl alcohol and diacetone alcohol; aromatic solvents such as xylene, benzene, toluene and ethylbenzene; alkanes such as hexanes and heptane; glycol ethers such as ethylene glycol monobutyl ether (butyl cellosolve), ethylene glycol monomethyl ether (2-methoxyethanol), ethylene glycol monoethyl ether (2-ethoxyethanol), ethylene glycol monopropyl ether (2-propoxyethanol), ethylene glycol monoisopropyl ether (2-isopropoxyethanol), ethylene glycol monophenyl ether (2-phenoxyethanol), ethylene glycol monobenzyl ether (2-benzyloxyethanol), diethylene glycol monomethyl ether (methyl carbitol), diethylene glycol monoethyl ether (carbitol cellosolve), diethylene glycol mono-n-butyl ether (2-(2-butoxyethoxy)ethanol), ethylene glycol dimethyl ether, ethylene glycol diethyl ether and ethylene glycol dibutyl ether; ethers such as tetrahydrofuran, dimethyl ether, diethyl ether; as well as amides such as NMP and DMF; as well as combinations thereof.

In various embodiments, the composition is comprised of at least one solvent selected from the group consisting of ketones, esters, carbonates, alcohols, alkanes, aromatics, ethers, amides and glycol ethers and combinations thereof. According to certain aspects of the invention, the at least one solvent is included in an amount sufficient to render the curable compositions described herein sufficiently flowable for application to a substrate. For example, in various embodiments of the invention, the compositions described herein have a viscosity of less than 4000 cPs or less than 3500 cPs or less than 3000 cPs or less than 2500 cPs, as measured at 25° C. using a Brookfield viscometer, model DV-II, using a 27 spindle (with the spindle speed varying typically between 50 and 200 rpm, depending on viscosity).

In particular embodiments, the at least one solvent is removed from the curable compositions described herein before curing by exposure to an energy source (radiation, heating) is initiated. For example, solvent may be removed by evaporation prior to energy-induced curing. If so desired, a substrate having one or more layers of the curable composition applied to a surface thereof may be heated and/or subjected to a flow of gas and/or placed under vacuum so as to facilitate solvent evaporation.

In certain embodiments of the invention, the curable composition is formulated to contain water, rather than non-reactive solvent. Such compositions may be referred to as water-borne systems, wherein one or more or all of the components of the composition are present as dispersions in water. Emulsifiers and/or dispersing agents may be employed to create and maintain stable aqueous dispersions of the composition components. One or more of the composition components may, in certain embodiments, be self-dispersing. Such a water-borne composition may be applied to the surface of a substrate, with the water serving to reduce the viscosity of the composition. The applied layer of the composition may then be treated to remove the water (by evaporation, for example), wherein the coating is thereafter cured (e.g., by heating and/or exposure to radiant energy). Curing of the free radical-polymerizable components of the composition, including the inventive monofunctional compound (for example, by irradiation of the coating by an appropriate energy source) may be conducted after evaporation of the water.

In certain embodiments of the invention, the compositions containing one or more inventive monofunctional compounds as described herein include at least one photoinitiator and are curable with radiant energy. For example, the photoinitiator(s) may be selected from the group consisting of α-hydroxyketones, phenylglyoxylates, benzyldimethylketals, α-aminoketones, mono-acyl phosphines, bis-acyl phosphines, phosphine oxides, metallocenes and combinations thereof. In particular embodiments, the at least one photoinitiator may be 1-hydroxy-cyclohexyl-phenyl-ketone and/or 2-hydroxy-2-methyl-1-phenyl-1-propanone. In other embodiments, the at least one photoinitiator is or includes a phosphine oxide, in particular bis(2,4-6-trimethylbenzoyl) phenyl phosphine oxide.

Suitable photoinitiators include, but are not limited to, 2-methylanthraquinone, 2-ethylanthraquinone, 2-chloroanthraquinone, 2-benzyanthraquinone, 2-t-butylanthraquinone, 1,2-benzo-9,10-anthraquinone, benzyl, benzoin, benzoin methyl ether, benzoin ethyl ether, benzoin isopropyl ether, alpha-methylbenzoin, alpha-phenylbenzoin, Michler's ketone, benzophenone, 4,4'-bis-(diethylamino) benzophenone, acetophenone, 2,2-diethyloxyacetophenone, diethyloxyacetophenone, 2-isopropylthioxanthone, thioxanthone, diethyl thioxanthone, 1,5-acetonaphthylene, ethyl-p-dimethylaminobenzoate, benzil ketone, α-hydroxy keto, 2,4,6-trimethylbenzoyldiphenyl phosphine oxide, benzyl dimethyl ketal, benzil ketal (2,2-dimethoxy-1,2-diphenylethanone), 1-hydroxycylclohexyl phenyl ketone, 2-methyl-1-[4-(methylthio) phenyl]-2-morpholinopropanone-1, 2-hydroxy-2-methyl-1-phenyl-propanone, oligomeric α-hydroxy ketone, phenylbis(2,4,6-trimethylbenzoyl)phosphine oxide, ethyl-4-dimethylamino benzoate, ethyl(2,4,6-trimethylbenzoyl)phenyl phosphinate, anisoin, anthraquinone, anthraquinone-2-sulfonic acid, sodium salt monohydrate, (benzene) tricarbonylchromium, benzil, benzoin isobutyl ether, benzophenone/1-hydroxycyclohexyl phenyl ketone, 50/50 blend, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino)benzophenone, camphorquinone, 2-chlorothioxanthen-9-one, dibenzosuberenone, 4,4'-dihydroxybenzophenone, 2,2-dimethoxy-2-phenylacetophenone, 4-(dimethylamino)benzophenone, 4,4'-dimethylbenzil, 2,5-dimethylbenzophenone,3,4-dimethylbenzophenone, diphenyl(2,4,6-trimethylbenzoyl)phosphine oxide/2-hydroxy-2-methylpropiophenone, 50/50 blend, 4'-ethoxyacetophenone, 2,4,6-trimethylbenzoyldiphenylphophine oxide, phenyl bis(2,4,6-trimethyl benzoyl) phosphine oxide, ferrocene, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, (cumene) cyclopentadienyl iron(ii) hexafluorophosphate, 9,10-diethoxy and 9,10-dibutoxyanthracene, 2-ethyl-9,10-dimethoxyanthracene, thioxanthen-9-one and combinations thereof.

The amount of photoinitiator is not considered to be critical, but may be varied as may be appropriate depending upon the photoinitiator(s) selected, the amount of free radical-polymerizable ethylenically unsaturated compound(s) present in the composition, the radiation source and the radiation conditions used, among other factors. Typically, however, the amount of photoinitiator may be from 0.05% to 5% by weight, based on the total weight of the composition (not including any water or non-reactive solvent that may be present).

In certain embodiments of the invention, the curable compositions described herein do not include any initiator and are curable with electron beam energy. In other embodiments, the compositions described herein include at least one free radical initiator that decomposes when heated or in the presence of an accelerator and are curable chemically (i.e., without having to expose the composition to radiation). The at least one free radical initiator that decomposes when heated or in the presence of an accelerator may, for example, comprise a peroxide or azo compound. Suitable peroxides for this purpose may include any compound, in particular any organic compound, that contains at least one peroxy (—O—O—) moiety, such as, for example, dialkyl, diaryl and aryl/alkyl peroxides, hydroperoxides, percarbonates, peresters, peracids, acyl peroxides and the like. The at least one accelerator may comprise, for example, at least one tertiary amine and/or one or more other reducing agents based on metal salts (such as, for example, carboxylate salts of transition metals such as iron, cobalt, manganese, vanadium and the like and combinations thereof). The accelerator(s) may be selected so as to promote the decomposition of the free radical initiator at room or ambient temperature to generate active free radical species, such that curing of the composition is achieved without having to heat or bake the composition. In other embodiments, no accelerator is present and the composition is heated to a temperature effective to cause decomposition of the free radical initiator and to generate free radical species which initiate curing of the free radical-polymerizable compound(s) present in the composition.

Thus, in various embodiments of the present invention, the compositions described herein are curable by techniques selected from the group consisting of radiation curing (UV radiation or electron beam curing), electron beam curing, chemical curing (using a free radical initiator that decomposes when heated or in the presence of an accelerator, e.g., peroxide curing), heat curing or combinations thereof.

The compositions of the present invention may optionally contain one or more additives instead of or in addition to the above-mentioned ingredients. Such additives include, but are not limited to, antioxidants, ultraviolet absorbers, photostabilizers, foam inhibitors, flow or leveling agents, colorants, pigments, dispersants (wetting agents), slip additives, fillers, thixotropic agents, matting agents, thermoplastics such as acrylic resins that do not contain any free radical-polymerizable functional groups, waxes or other various additives, including any of the additives conventionally utilized in the coating, sealant, adhesive, molding or ink arts.

EXAMPLES

Example 1

Preparation of Monofunctional Urethane

This example demonstrates the preparation of a monofunctional urethane acrylate in accordance with the present invention based on hydroxyethyl acrylate (HEA), isophorone diisocyanate (IPDI) and tricyclodecane methanol (TCDM). In a first step, 220 g of IPDI (Desmodur® I, manufactured by Covestro), 0.86 g Irganox® 1035 stabilizer (manufactured by BASF) and 0.35 g dibutyltin dilaurate catalyst (from Sigma-Aldrich) were placed in a reaction vessel. 116 g HEA (manufactured by Nippon Shokubai) were slowly added to the reaction vessel with stirring. The contents of the reaction vessel were kept under 60° C. by controlling the rate at which the HEA was added and/or by cooling the reaction vessel with a water bath. After addition of the HEA is completed, the mixture was held at 60° C. for another hour. The reaction mixture at this point contained the following intermediate product (II), wherein IP is an isophorone moiety:

$$H_2C=CHC(=O)OCH_2CH_2OC(=O)NH-IP-NCO \qquad (II)$$

An air sparge was applied and 166 g TCDM (TCD Alcohol M, manufactured by Oxea) were then slowly added to the reaction mixture with stirring at a rate effective to keep the temperature of the reaction mixture below 80° C. The reaction mixture was then held at 80° C. with stirring after the addition of TCDM was completed until the residual isocyanate content dropped below 0.06 wt %. The product obtained was a clear liquid having a viscosity of 9300 mPa·s (cP) at 75° C. The reaction product contained a monofunctional urethane acrylate having the following structure (Ill), wherein IP is an isophorone moiety and TCD is a tricyclodecane moiety:

$$H_2C=CHC(=O)OCH_2CH_2OC(=O)NH-IP-NHC(=O)OCH_2-TCD \quad (III)$$

Example 2

This example describes the preparation and curing of formulations containing monofunctional compounds in accordance with the present invention.

The following components were used:
CN991 aliphatic polyester-based urethane diacrylate oligomer (Sartomer USA, LLC).
SR833S tricyclodecane dimethanol diacrylate (Sartomer USA, LLC).
SR531 cyclic trimethyolpropane formal acrylate (Sartomer USA, LLC).
Monofunctional Urethane Acrylate A: prepared in accordance with Example 1.
Monofunctional Urethane Acrylate B and C: reaction product of tricyclodecane dimethanol monoacrylate, dicyclohexylmethane diisocyanate, tricyclodecane dimethanol and tricyclodecane methanol.
Irgacure® 819 photoinitiator (BASF).
Formulation 2-A and 2-B each contained 40 parts by weight CN991, 30 parts by weight SR833S, 10 parts by weight SR531 and 0.5 parts by weight Irgacure® 819 photoinitiator. Formulation 2-A additionally contained 20 parts by weight Monofunctional Urethane Acrylate A, Formulation 2-B additionally contained 20 parts by weight Monofunctional Urethane Acrylate B and Formulation 2-C additionally contained 20 parts by weight Monofunctional Urethane Acrylate C.
Formulation Testing Protocol Each combination was prepared through standard heating and mixing practices. Once formulations are completely homogenous and thoroughly mixed, viscosity measurements are typically the first performance criteria to be taken. Viscosity measurements are performed using a Brookfield cup-and-bob style viscometer in which ample time is provided to reach a stable temperature and viscosity readout.

Molds were cast in silicone rubber to prepare samples for each mechanical test. Blends were poured into molds to create the shapes according to ASTM D638 for tensile testing, ASTM D256 for IZOD impact resistance, ASTM D2240 for shore hardness or ISO78 for flexural tests. Once the blends are cast into the molds, they are then cured through exposure to ultraviolet light. 100 fpm (0.508 m/s) line speed with a 600 W/in² (930 kW/m²) V-Bulb spectrum was used to cure the example formulations. Cured samples are removed from the mold and may undergo additional polishing and notching for specific testing.

Tensile test controls around strain rate, pre-load and toe compensation are according to ASTM D638. Breaks are expected within the gauge length and material failure beyond the gauge lengths are excluded from the sample population. Typical sample population is greater than (3) three samples per formulation. Modulus, strength, elongation and energy to break values are all outlined in and are in accordance with ASTM D638.

Impact test controls around hammer selection and sample preparation are according to ASTM D256. Breaks are expected to be complete breaks, with any partial breaks or tears being excluded from the sample population. Sample population is greater than (5) five samples per formulation. Impact strength values in joules/meter are recorded and calculated in accordance to ASTM D256.

Shore hardness measurements according to ASTM D2240 were performed on a sample population of (3) test specimens. Samples with improper levels of cure were excluded and values were recorded on the Shore D scale for hardness.

Flexural testing for modulus and flexural strength values were according to ISO-78. Breaks or maximum flexural strengths were expected within 5% deflection, deviations from this excluded the samples from the population. Modulus and strength values were calculated according to the ISO standard and recorded for comparison.

The results obtained are shown in Table 1:

TABLE 1

| | Example 2-A | Example 2-B | Example 2-C |
|---|---|---|---|
| Viscosity before curing at 25° C. (cP or mPa · s) | 2120 | 4900 | 6628 |
| Tensile Properties (ASTM D638, Type IV Dogbones) | | | |
| Strength (psi) | 4,400 | 7,690 | 8,050 |
| Elongation (%) | 22.3 | 7.3 | 8.5 |
| Modulus (psi) | 70,277 | 138,062 | 134,175 |
| Izod Impact Resistance (ASTM D256, Notched Samples) | | | |
| Resistance (J/m) | 18.5 | 40.8 | 42.7 |
| Flexural Strength using 3-Point Bending (ISO 78) | | | |
| Flexural Strength (psi/MPa) | 12,500/86.2 | 12,589/87.8 | 13,938/96.1 |
| Elastic Modulus (psi/MPa) | 290,700/2004 | 304,000/2096 | 312,311/2153 |

Example 3

Additional testing was performed to examine how a monofunctional urethane acrylate in accordance with the present invention performs in combination with other types of (meth)acrylic monomers. Formulations were prepared as shown in Table 2, generally following the protocol of Example 2; the listed amounts of the formulation components are in parts by weight.

The following components were used:

Monofunctional urethane acrylate: Prepared in accordance with Example 1.

SR256: 2(2-ethoxyethoxy) ethyl acrylate (Sartomer USA, LLC).

SR730: ethyl triglycol methacrylate (Sartomer USA, LLC).

SR423: isobornyl methacrylate (Sartomer USA, LLC).

CN131: aromatic monoacrylate oligomer (Sartomer USA, LLC).

SR454: ethoxylated (3) trimethylolpropane triacrylate (Sartomer USA, LLC).

SR531: cyclic trimethylolpropane formal acrylate (Sartomer USA, LLC).

SR833: tricyclododecane dimethanol diacrylate.

Irgacure® 819 photoinitiator (BASF).

Good compatibility between many types of traditional acrylic monomers and the inventive monofunctional urethane acrylate was found. The physical properties of the formulations after being cured are shown in Table 2.

TABLE 2

|  | 3A | 3B | 3C | 3D |
|---|---|---|---|---|
| Mono-functional Urethane Acrylate | 40 | 40 | 40 | 40 |
| SR256 | 30 | | | |
| SR730 | 30 | | | |
| SR423 | | 30 | | |
| CN131 | | 30 | | |
| SR454 | | | 30 | |
| SR531 | | | 30 | 30 |
| SR833 | | | | 30 |
| Additional Photoinitiator Package | | | | |
| Irgacure ® 819 | 0.5 | 0.5 | 0.5 | 0.5 |
| Brookfield Viscosity Results-Cup and Bob style Viscometer | | | | |
| Viscosity @ 25° C. (cP or mPa · s) | 70 | 1000 | 330 | 600 |
| ASTM D638-Tensile Properties using Type IV Dogbones | | | | |
| Strength (psi/MPa) | 110/ 0.758 | 5,650/ 39.0 | 4,680/ 32.3 | 1,310/ 9.03 |
| Elongation (%) | 12.0 | 1.2 | 2.8 | 0.8 |
| Modulus (psi) | 300/ 2.07 | 120,450/ 830 | 131,600/ 907 | 59,080/ 407 |

The invention claimed is:

1. A compound having a structure in accordance with Formula (I):

$$Q\text{-}(R^1Z^1)_m\text{—}RZ \qquad (I)$$

wherein Q is a moiety containing a single free radical-polymerizable functional group, R is a urethane/ureido-containing structural unit, Z is a monovalent moiety containing at least one cyclic structural element, each $R^1$, if present, is independently selected to be a urethane/ureido-containing structural unit which is the same as or different from R, each $Z^1$, if present, is independently selected to be a divalent moiety containing at least one cyclic structural element and m is 0 or an integer of 1 or more and wherein the compound has at least two urethane and/or ureido linkages per molecule and the single free radical-polymerizable functional group in Q is a mono-ethylenically unsaturated functional group.

2. The compound of claim 1, wherein the mono-ethylenically unsaturated functional group is selected from the group consisting of allyl groups and (meth)acrylate groups.

3. The compound of claim 1, wherein Q is a group having structure $H_2C\!=\!C(R^2)C(\!=\!O)\text{—}O\text{—}R^3\text{—}$, with $R^2\!=\!H$, $CH_3$ or $CH_2CH_3$ and $R^3\!=\!a$ $C_2$ to $C_6$ linear or branched alkylene group, an oligoether moiety or an oligoester moiety.

4. The compound of claim 1, wherein Q has structure $H_2C\!=\!CH\text{—}C(\!=\!O)OCH_2CH_2\text{—}$.

5. The compound of claim 1, wherein m is 0 or an integer from 1 to 10.

6. The compound of claim 1, wherein Z is a monovalent moiety containing at least one cyclic structural element selected from the group consisting of aromatic groups and alicyclic groups.

7. The compound of claim 1, wherein Z is a monovalent moiety containing at least one alicyclic structural element selected from the group consisting of monocyclic, bicyclic, tricyclic, tetracyclic, pentacyclic and hexacyclic hydrocarbon radicals.

8. The compound of claim 1, wherein Z is a monovalent moiety containing a tricyclodecane radical.

9. The compound of claim 1, wherein m is an integer of 1 or greater than 1 and each $Z^1$ independently is a divalent moiety containing at least one cyclic structural element selected from the group consisting of aromatic groups and alicyclic groups.

10. The compound of claim 1, wherein m is an integer of 1 or more and each $Z^1$ independently is a divalent moiety containing at least one alicyclic structural element selected from the group consisting of monocyclic, bicyclic, tricyclic, tetracyclic, pentacyclic and hexacyclic hydrocarbon radicals.

11. The compound of claim 1, wherein m is an integer of 1 or more and each $Z^1$ independently is a divalent moiety containing a tricyclodecane radical.

12. The compound of claim 1, wherein each R and $R^1$, if present, independently has structure —O—C(=O)NH—$R^3$—NH—C(=O)—O—, with $R^3$ being a divalent hydrocarbon radical.

13. A curable composition comprised of at least one compound in accordance with claim 1 and at least one additional ethylenically unsaturated monomer or oligomer.

14. The curable composition of claim 13, wherein the at least one additional ethylenically unsaturated monomer or oligomer includes at least one compound selected from the group consisting of (meth)acrylates.

15. The curable composition of claim 13, additionally comprising at least one additive selected from the group consisting of initiators, stabilizers and fillers.

16. A cured composition which results from the curable composition of claim 13.

17. An article comprising a cured composition in accordance with claim 16.

18. The article of claim 17, wherein the article is a three-dimensional article, a coated article, a laminated article or a printed article.

19. A method of making a compound in accordance with claim 1, comprising the steps of:
    a) reacting a mono-hydroxyl or mono-amino functional compound containing a single free radical-polymerizable functional group with a diisocyanate in a stoichiometry effective to yield an intermediate product which is a 1:1 adduct of the mono-hydroxyl or mono-amino functional compound containing a single free radical-polymerizable functional group and the diisocyanate and which contains a single free radical-polymerizable functional group, a single isocyanate group and a urethane or ureido linkage;
    b) reacting the intermediate product with a mono-hydroxyl or mono-amino functional compound containing at least one cyclic structural element.

20. A method of making a compound in accordance with claim 1, comprising the steps of:
    a) reacting i) a mono-hydroxyl or mono-amino functional compound containing a single free radical-polymerizable functional group, ii) a diisocyanate and iii) a di-hydroxyl, di-amino or mono-hydroxy and mono-amino functional compound containing at least one cyclic structural element in a stoichiometry effective to yield an intermediate product which is a 1:X:Y adduct of the mono-hydroxyl or mono-amino functional compound containing a single free radical-polymerizable functional group, the diisocyanate and the di-hydroxyl, di-amino or mono-hydroxy and mono-amino functional compound containing at least one cyclic structural element and which contains a single free radical-polymerizable functional group, a single isocyanate group and two or more urethane or ureido linkages, wherein X is an integer of 1 or more and represents the number of moles of di-hydroxyl, di-amino or mono-hydroxy and mono-amino functional compound containing at least one cyclic structural element incorporated in the adduct per mole of mono-hydroxyl or mono-amino functional compound containing a single free radical-polymerizable functional group and Y=X+1 and represents the number of moles of diisocyanate incorporated in the adduct per mole of mono-hydroxyl or mono-amino functional compound containing a single free radical-polymerizable functional group;

b) reacting the intermediate product with a mono-hydroxyl or mono-amino functional compound containing at least one cyclic structural element.

21. A method of making a compound in accordance with claim 1, comprising the steps of:
a) reacting a mono-hydroxyl or mono-amino functional compound containing at least one cyclic structural element with a diisocyanate in a stoichiometry effective to yield an intermediate product which is a 1:1 adduct of the mono-hydroxyl or mono-amino functional compound containing at least one cyclic structural element and the diisocyanate and which contains at least one cyclic structural element, a single isocyanate group and a urethane or ureido linkage;
b) reacting the intermediate product with a mono-hydroxyl or mono-amino functional compound containing a single free radical-polymerizable functional group.

22. A method of making a compound in accordance with claim 1, comprising the steps of:
a) reacting i) a mono-hydroxyl or mono-amino functional compound containing at least one cyclic structural element, ii) a diisocyanate and iii) a di-hydroxyl, di-amino or mono-hydroxy and mono-amino functional compound containing at least one cyclic structural element in a stoichiometry effective to yield an intermediate product which is a 1:X:Y adduct of the mono-hydroxyl or mono-amino functional compound containing at least one cyclic structural element, the diisocyanate and the di-hydroxyl, di-amino or mono-hydroxy and mono-amino functional compound containing at least one cyclic structural element and which contains at least two cyclic structural elements, a single isocyanate group and two or more urethane or ureido linkages, wherein X is an integer of 1 or more and represents the number of moles of di-hydroxyl, di-amino or mono-hydroxy and mono-amino functional compound containing at least one cyclic structural element incorporated in the adduct per mole of mono-hydroxyl or mono-amino functional compound containing at least one cyclic structural element and Y=X+1 and represents the number of moles of diisocyanate incorporated in the adduct per mole of mono-hydroxyl or mono-amino functional compound containing at least one cyclic structural element;

b) reacting the intermediate product with a mono-hydroxyl or mono-amino functional compound containing a single free radical-polymerizable functional group.

23. A method of making a cured composition comprising curing a curable composition as defined in claim 13.

24. A method of making a three-dimensional article, comprising the steps of:
a) coating a first layer of a composition comprising at least one compound in accordance with claim 1 onto a surface;
b) curing the first layer to provide a cured first layer;
c) coating a second layer of the composition onto the cured first layer;
d) curing the second layer to provide a cured second layer adhered to the cured first layer; and
e) repeating steps c) and d) a desired number of times to build up the three-dimensional article.

25. The method of claim 24, wherein the curing steps are performed by exposing the layer of the composition to radiation.

26. A composition selected from a coating, an adhesive, a sealant, an ink, a 3D printing resin or a molding resin comprising a compound as defined in claim 1.

* * * * *